(12) United States Patent
Mulcahy et al.

(10) Patent No.: US 9,440,037 B2
(45) Date of Patent: Sep. 13, 2016

(54) ACCLIMATIZATION THERAPY FOR FIRST TIME USERS

(71) Applicant: RESMED LIMITED, Bella Vista, New South Wales (AU)

(72) Inventors: David Mulcahy, Castle Hill (AU); Philip Rodney Kwok, Chatswood (AU); William Mcinnes Somerville, Hornsby (AU); David Richard Vorreiter, Carlingford (AU)

(73) Assignee: RESMED LIMITED, Bella Vista, New South Wales (AU)

( * ) Notice: Subject to any disclaimer, the term of this patent is extended or adjusted under 35 U.S.C. 154(b) by 143 days.

(21) Appl. No.: 13/961,483

(22) Filed: Aug. 7, 2013

(65) Prior Publication Data

US 2013/0319415 A1    Dec. 5, 2013

Related U.S. Application Data

(62) Division of application No. 12/230,881, filed on Sep. 5, 2008, now Pat. No. 8,528,551.

(60) Provisional application No. 60/935,885, filed on Sep. 5, 2007.

(51) Int. Cl.
| | |
|---|---|
| *F16K 31/02* | (2006.01) |
| *A61M 16/00* | (2006.01) |
| *A62B 7/00* | (2006.01) |
| *A61M 16/06* | (2006.01) |
| *A61M 16/08* | (2006.01) |

(52) U.S. Cl.
CPC ..... *A61M 16/0066* (2013.01); *A61M 16/0051* (2013.01); *A61M 16/0069* (2014.02); *A61M 16/06* (2013.01); *A61M 16/0875* (2013.01); *A61M 2016/0021* (2013.01); *A61M 2016/0027* (2013.01); *A61M 2016/0036* (2013.01); *A61M 2205/502* (2013.01); *A61M 2205/52* (2013.01)

(58) Field of Classification Search
CPC ............... A61M 16/0051; A61M 2016/0015
USPC ...................... 128/204.21–204.23
See application file for complete search history.

(56) References Cited

U.S. PATENT DOCUMENTS

| | | |
|---|---|---|
| 5,199,424 A | 4/1993 | Sullivan et al. |
| 5,245,995 A | 9/1993 | Sullivan et al. |
| 5,485,851 A | 1/1996 | Erickson |
| 5,522,382 A | 6/1996 | Sullivan et al. |
| 5,704,345 A | 1/1998 | Berthon-Jones |
| 5,823,187 A | 10/1998 | Estes et al. |

(Continued)

FOREIGN PATENT DOCUMENTS

| | | |
|---|---|---|
| WO | WO 01/05460 A1 | 1/2001 |
| WO | WO 01/97893 | 12/2001 |
| WO | WO 03/057025 A2 | 7/2003 |

*Primary Examiner* — Kristen Matter
(74) *Attorney, Agent, or Firm* — Nixon & Vanderhye P.C.

(57) ABSTRACT

Systems, methods, and/or apparatuses for acclimatizing a user to positive airway pressure (PAP) therapy are provided. Generally, a sub-therapeutic treatment pressure is provided initially. It may be ramped up to a full treatment pressure over the course of one or more therapy sessions. The pressure level may be ramped up based on, for example, sleep state, sleep phase, patient compliance with types of treatment (e.g. bilevel vs. CPAP, etc.), clinician input (either at the site, remotely, via pre-programmed smartcards, etc.), etc. Such techniques may be used alone or in combination.

17 Claims, 8 Drawing Sheets

(56) References Cited

U.S. PATENT DOCUMENTS

| | | |
|---|---|---|
| 5,944,680 A | 8/1999 | Christopherson et al. |
| 5,947,115 A | 9/1999 | Lordo et al. |
| 6,029,665 A | 2/2000 | Berthon-Jones |
| 6,112,746 A | 9/2000 | Kwok et al. |
| 6,138,675 A | 10/2000 | Berthon-Jones |
| 6,357,441 B1 | 3/2002 | Kwok et al. |
| 6,363,933 B1 | 4/2002 | Berthon-Jones |
| 6,397,845 B1 | 6/2002 | Burton |
| 6,398,739 B1 | 6/2002 | Sullivan et al. |
| 6,401,713 B1 | 6/2002 | Hill |
| 6,581,602 B2 | 6/2003 | Kwok et al. |
| 6,634,358 B2 | 10/2003 | Kwok et al. |
| 6,635,021 B1 | 10/2003 | Sullivan et al. |
| 6,641,542 B2 | 11/2003 | Cho et al. |
| 7,011,087 B1 | 3/2006 | Sullivan |
| 7,089,936 B2 | 8/2006 | Madaus et al. |
| 7,225,809 B1 | 6/2007 | Bowen |
| 7,252,640 B2 | 8/2007 | Ni et al. |
| 7,607,432 B2 | 10/2009 | Sullivan |
| 7,640,055 B2 | 12/2009 | Geva et al. |
| 7,806,831 B2 | 10/2010 | Lavie et al. |
| 8,281,787 B2 | 10/2012 | Burton |
| 2005/0005937 A1* | 1/2005 | Farrugia .................. A61B 5/08 128/204.18 |
| 2005/0038353 A1* | 2/2005 | Rapoport et al. ............. 600/532 |
| 2006/0084877 A1* | 4/2006 | Ujhazy ............. A61M 16/0051 600/483 |
| 2006/0249149 A1 | 11/2006 | Meier et al. |
| 2007/0208269 A1 | 9/2007 | Mumford et al. |
| 2008/0202528 A1* | 8/2008 | Carter ............... A61M 16/0051 128/204.23 |
| 2009/0038616 A1 | 2/2009 | Mulcahy et al. |

* cited by examiner

ACCLIMATIZATION THERAPY FOR FIRST TIME USERS

CROSS REFERENCE TO APPLICATIONS

This application is a divisional of U.S. application Ser. No. 12/230,881, filed Sep. 5, 2008 and now allowed; which claims the benefit of U.S. Provisional Application No. 60/935,885, filed Sep. 5, 2007, the contents of each being incorporated by reference in its entirety. This application also incorporates by reference in its entirety each of PCT Application No. PCT/AU06/00822, filed Jun. 14, 2006, Australian Application No. AU2005903089, filed Jun. 14, 2005, Australian Application No. AU2005906122, filed Nov. 4, 2005, and Australian Application No. AU2005906193.

FIELD OF THE INVENTION

The example embodiments described herein relate to mechanical ventilation of sleep disordered breathing (SDB), and in particular to methods and apparatus for improving patient compliance in Continuous Positive Airway Pressure (CPAP) treatment.

BACKGROUND OF THE INVENTION

A comprehensive background discussion of mechanical ventilation can be found in "Principles and Practice of Mechanical Ventilation" (1994) edited by Martin J. Tobin, published by McGraw-Hill Inc., ISBN 0-07-064943-7.

The use of nasal Continuous Positive Airway Pressure (CPAP) to treat Obstructive Sleep Apnea (OSA) was invented by Colin Sullivan, see U.S. Pat. No. 4,944,310. Generally, the treatment involves providing a supply of air or breathable gas from a blower (sometimes referred to as a flow generator) to a patient via an air delivery conduit (e.g. a flexible tube) and a patient interface, such as, for example, a full-face or nasal mask, or nasal prongs. While treatment is effective, some patients find it uncomfortable. Improving patient comfort and compliance is a continuing challenge.

One way to improve comfort is to provide a more comfortable patient interface. In this regard, the ResMed MIRAGE™ masks have provided significant improvement in comfort. See U.S. Pat. Nos. 6,112,746; 6,357,441; 6,581, 602; and 6,634,358. A more recent development is the ResMed MIRAGE™ ACTIVA™ mask series. See International Patent Application WO 2001/97893.

In the early days of nasal CPAP systems for treating OSA, patients were first titrated in a clinical study to determine an optimal treatment pressure. Titration involves a patient sleeping overnight in a clinic and being tested with a mask and CPAP device. The treatment pressure provided by the CPAP device is adjusted until apneas are eliminated. The treatment pressure is usually in the range of 4-20 cmH$_2$O. A device would be set to that pressure and given to the patient to take home. A subsequent development was the automatically adjusting device that a patient could take home. The automatically adjusting device will raise and/or lower the treatment pressure based on indications of obstructive sleep apnea, such as snoring. Such CPAP devices are sometime generically referred to as Automatic Positive Airway Pressure (APAP) devices. See U.S. Pat. Nos. 5,245,995; 6,398, 739; and 6,635,021.

Another form of automatically adjusting CPAP device is the ResMed AUTOSET™ SPIRIT™ device. In this device, the CPAP pressure is automatically increased or decreased at least during patient inspiration in accordance with indications of flow limitation, such as flow flattening, snore, apnea, and hypopnea. See U.S. Pat. Nos. 5,704,345; 6,029,665; 6,138,675; and 6,363,933. An advantage of an automatically adjusting system is that over time the treatment pressure required may vary for a particular patient and a correctly functioning automatic system can obviate the need for the patient to return for a subsequent sleep study. These patents also describe a method and apparatus for distinguishing between so-called "central" and obstructive apneas.

Another type of nasal CPAP device provides a first pressure during inhalation (sometimes termed an IPAP) and a second, lower pressure during exhalation (sometimes termed an EPAP). Examples of these include the ResMed VPAP™ series, and the Respironics BiPAP series. Bilevel CPAP devices may be prescribed for patients who do not comply with single pressure CPAP devices. Some patients perceive that the lower pressure during exhalation is more comfortable, at least while they are awake.

Another way of improving patient comfort and compliance is to start each therapy session at a low therapeutic pressure, e.g., 4 cmH$_2$O, and ramp up to full therapeutic pressure over the first hour, to allow the patient to adjust to the sensation while falling asleep. Alternatively, the device may set to implement a time delay before full therapeutic pressure is applied, to allow the patient time to fall asleep before full therapeutic pressure is applied. See U.S. Pat. Nos. 5,199,424 and 5,522,382.

The contents of all of the aforesaid patents are incorporated herein by cross-reference in their entireties.

Some OSA patients find treatment with the above devices uncomfortable and they become non-compliant with the therapy. Other patients such as cardiovascular patients with Congestive Heart Failure, patients with REM Hypoventilation, and patients with Respiratory Insufficiency could also benefit from a more comfortable and/or effective form of therapy.

One hurdle in patient compliance occurs in the initial stages of treatment, where a patient may have difficulty in adjusting to the sensations of the therapy and may quit therapy before realizing the benefits of the therapy.

A further hurdle to patient acceptance of the therapy is in the initial fitting of the patient interface (e.g., mask), where the mask fit is tested under relatively low pressure and high flow. This may result in noisy operation of the device and high flow air leaks as the mask is adjusted to the patient, which can be a noisy and unsettling initial experience for the patient.

Other impediments to patient comfort and compliance include the treatment impeding the ability of the patient to communicate to the clinician or bed partner, or the patient or bed partner being disturbed by air leaks from the mask.

SUMMARY OF THE INVENTION

One aspect of the invention relates to a method and apparatus to overcome or ameliorate one or more of these disadvantages.

In certain example embodiments, a method of acclimatizing a patient to CPAP therapy for treatment of sleep-disordered breathing is provided. A device configured to supply pressurized breathable gas to the patient may be provided. At least one smartcard also may be provided, with each smartcard having treatment parameters stored thereon. The device may be configured to accept the at least one smartcard and to provide the supply of pressurized breathable gas based on the treatment parameters stored thereon.

In certain example embodiments, a CPAP device for acclimatizing a patient to treatment of sleep-disordered breathing is provided. The CPAP device may be operable to provide a supply pressurized breathable gas to the patient based on treatment parameters stored on a smartcard, with the smartcard being readable by the CPAP device.

In certain example embodiments, a smartcard for use with a device operable to provide a supply of pressurized breathable gas to a patient is provided, with the smartcard having treatment parameters stored thereon, and the treatment parameters comprising a pressure setting to be supplied to the device.

Certain example embodiments provide a method of acclimatizing a patient to CPAP therapy for treatment of sleep-disordered breathing. A device configured to supply pressurized breathable gas to the patient may be provided. Target CPAP treatment parameters to be used when treating the patient may be identified, with the target CPAP treatment parameters comprising a full treatment pressure to be delivered to the patient during patient inspiration and patient expiration. A bilevel treatment may be provided, with the bilevel treatment comprising providing IPAP therapy and/or EPAP therapy. Parameters associated with the IPAP therapy and/or parameters associated with the EPAP therapy may be ramped up until the target CPAP treatment parameters are met.

Certain example embodiments provide a PAP device for acclimatizing a patient to treatment of sleep-disordered breathing. A flow generator may be operable in acclimatization and CPAP modes to provide a supply of pressurized breathable gas to the patient. A controller may be operable to instruct the flow generator, in the acclimatization mode, to provide the breathable gas at a first pressure during patient inspiration, and to provide the breathable gas at a second pressure during patient expiration, with the second pressure being different from the first pressure. The controller may be operable to adjust the first pressure and/or the second pressure until a target CPAP therapy is provided at which point the flow generator operates in the CPAP mode, with the target CPAP therapy having a full treatment pressure to be delivered to the patient during patient inspiration and patient expiration associated therewith.

In certain other example embodiments, a method of acclimatizing a patient to therapy for treatment of sleep-disordered breathing is provided. At least one parameter of the patient may be continuously monitored. The at least one parameter may be associated with a continuously adjusting treatment pressure for the patient. A supply of pressurized breathable gas may be provided to the patient at a continuously adjusting pressure based on the at least parameter. The breathable gas initially may be provided at an adjustable limited pressure, with the limited pressure being below the treatment pressure. The limited pressure may be ramped up during the treatment until the limited pressure equals the treatment pressure.

In certain other example embodiments, a PAP device for acclimatizing a patient to treatment of sleep-disordered breathing is provided. A monitor may be operable to continuously monitor at least one parameter of the patient. A processor may be operable to associate the at least one parameter with a continuously adjusting treatment pressure. A flow generator may be operable to provide a supply of pressurized breathable gas to the patient at a continuously adjusting pressure based on the at least one parameter. The flow generator may be configured to provide the breathable gas at the treatment pressure and at a limited pressure, with the limited pressure being below the treatment pressure. The flow generator may be operable to ramp up the limited pressure until the limited pressure equals the treatment pressure.

Certain example embodiments provide a method of acclimatizing a patient to therapy for treatment of sleep-disordered breathing. At least one parameter of the patient may be monitored. The at least one parameter may be associated with a treatment pressure for the patient. A supply of pressurized breathable gas at the treatment pressure may be provided to the patient. One or more obstructive events during the treatment may be detected. For each obstructive event detected, the treatment pressure may be incrementally increased a predetermined amount.

Certain example embodiments provide a PAP device for acclimatizing a patient to treatment of sleep-disordered breathing. A monitor may be operable to monitor at least one parameter of the patient and operable to detect one or more obstructive events during treatment. A processor may be operable to associate the at least one parameter with a treatment pressure. A flow generator may be operable to provide a supply of pressurized breathable gas to the patient. The flow generator may be configured to incrementally increase the treatment pressure a predetermined amount for each obstructive event detected by the monitor.

Still further example embodiments relate to a method of acclimatizing a patient to therapy for treatment of sleep-disordered breathing. The patient may be observed to determine a full treatment pressure appropriate for the patient. A limited treatment pressure less than the full treatment pressure may be determined. A supply of pressurized breathable gas may be provided to the patient at the limited treatment pressure. At least one parameter of the patient may be monitored, with the at least one parameter corresponding to patient acceptance of the treatment. The at least one parameter may be communicated to a sleep clinician via a computer-mediated communication channel, the sleep clinician being located remote from the patient.

Still further example embodiments relate to a system for acclimatizing a patient to therapy for treatment of sleep-disordered breathing. A flow generator may be operable to provide a supply of pressurized breathable gas to the patient at a plurality of pressures. A sensor may be operable to monitor at least one parameter of the patient. A first communicator may be operable to send the at least one parameter to a sleep clinician, and may be further operable to receive at least one treatment parameter from the sleep clinician. The sleep clinician may be located remote from the patient. The pressure of the breathable gas initially may be provided at a limited treatment pressure less than a full treatment pressure appropriate for the patient.

In still further example embodiments, a method of acclimatizing a patient to therapy for treatment of sleep-disordered breathing is provided. A supply of pressurized breathable gas is provided through a tube to a mask, with the mask having an opening therein, and with the opening allowing controlled mask leak. A size of the opening may be adjusted to alter an amount of mask leak and cause a corresponding change in the breathable gas pressure. The size of the opening may be adjusted to vary a pressure of the breathable gas between a full treatment pressure and a limited pressure, with the limited pressure being less than the full treatment pressure.

In still further example embodiments, a mask for use by a patient during therapy for treatment of sleep-disordered breathing is provided. The mask may be configured to receive a supply of pressurized breathable gas from a tube connected to a flow generator. An opening may allow controlled mask leak. An adjustment mechanism may adjust a size of the opening to alter an amount of mask leak and for causing a corresponding change in the breathable gas' pressure. The size of the opening may be configured to be adjusted to vary a pressure of the breathable gas between a full treatment pressure and a limited pressure, with the limited pressure being less than the full treatment pressure.

In still further example embodiments, a system for acclimatizing a patient to therapy for treatment of sleep-disordered breathing is provided. A flow generator may be operable to provide a supply of pressurized breathable gas to the patient through a flexible tube connected to a mask. The mask may comprise an opening, the opening allowing controlled mask leak; and an adjustment mechanism for adjusting a size of the opening to alter an amount of mask leak and for causing a corresponding change in the breathable gas' pressure. The size of the opening may be configured to be adjusted to vary a pressure of the breathable gas between a full treatment pressure and a limited pressure, with the limited pressure being less than the full treatment pressure.

Certain example embodiments provide a method of acclimatizing a patient to therapy for treatment of sleep-disordered breathing. A plurality of full treatment pressures may be provided, with each full treatment pressure being associated with a sleep stage. The sleep stage of the patient may be determined. A supply of pressurized breathable gas may be provided to the patient in dependence on the sleep stage of the patient.

Certain example embodiments provide a PAP device for acclimatizing a patient to therapy for treatment of sleep-disordered breathing. A sensor for determining a sleep stage of the patient may be provided, with each sleep stage having a treatment pressure associated therewith. A flow generator may be operable to provide a supply of pressurized breathable gas to the patient in dependence on the sleep stage of the patient and configured to adjust the treatment pressure of the breathable gas if the sensor determines that the sleep stage of the patient changes.

Certain other example embodiments provide a method of acclimatizing a patient to therapy for treatment of sleep-disordered breathing. A supply of pressurized breathable gas may be provided to the patient for a predetermined settling time at a limited pressure. The breathable gas may be provided at a full treatment pressure after the predetermined settling time. The limited pressure may be lower than the full treatment pressure.

Certain other example embodiments provide a system for acclimatizing a patient to therapy for treatment of sleep-disordered breathing. A flow generator may be operable to provide a supply of pressurized breathable gas to the patient for a predetermined settling time at a limited pressure and operable to provide the breathable gas at a full treatment pressure after the predetermined settling time. The limited pressure may be lower than the full treatment pressure.

Still other example embodiments provide a method of acclimatizing a patient to therapy for treatment of sleep-disordered breathing. The patient may be treated using a PAP device. Patient compliance data may be compiled during the treatment. The patient compliance data may be processed to identify problems associated with the treatment. Any identified problems may be compared to a solutions database.

Still other example embodiments provide a system for acclimatizing a patient to therapy for treatment of sleep-disordered breathing. A PAP device may be operable to provide a supply of pressurized breathable gas to the patient. A computer-mediated compliance monitoring package may be operable to execute the following steps of compiling patient compliance data during the treatment; processing the patient compliance data to identify problems associated with the treatment; and, comparing any identified problems to a solutions database.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

1. Illustrative Hardware

A positive airway pressure (PAP) device in accordance with an embodiment of the invention includes a blower and blower-controller. The blower can deliver a supply of air at positive pressure 2-40 $cmH_2O$, but generally delivers the breathable gas in the range of 4-20 $cmH_2O$ to a patient interface via an air delivery conduit.

The device also includes a flow sensor to measure the flow of air along the conduit, and pressure sensors to measure the pressure of air at the blower outlet.

In one form, the device alternatively includes an additional pressure sensor to detect the pressure in the patient interface.

Figure 1:
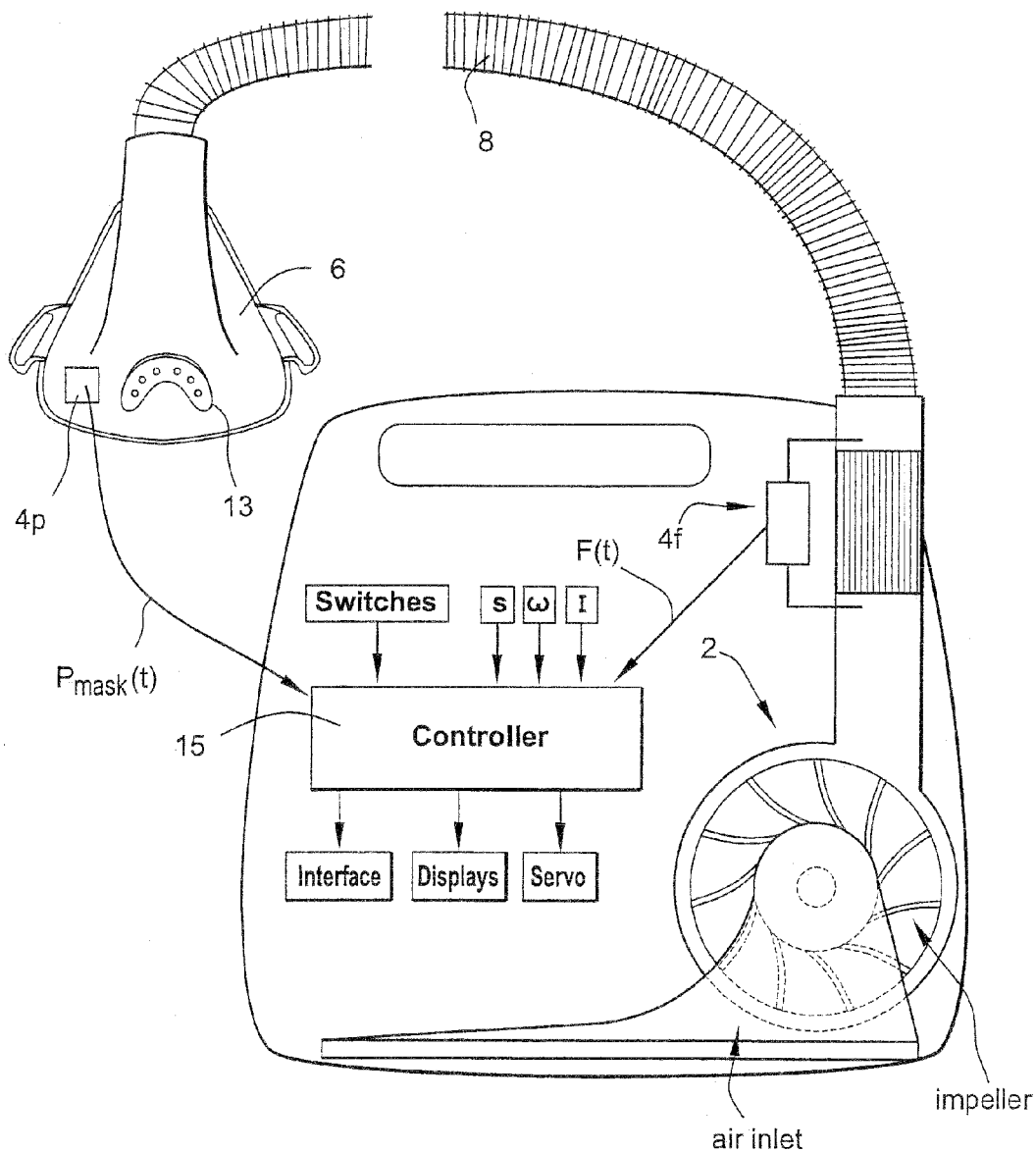
FIG. 1 illustrates a ventilator apparatus according to an example embodiment for implementing certain illustrative methods.

For example, FIG. 1 illustrates a ventilator device according to an example embodiment. As illustrated, the ventilator device may include a servo-controlled blower 2, a flow sensor 4f, pressure sensor 4p, a mask 6, and an air delivery conduit 8 for connection between the blower 2 and the mask 6. Exhaust gas is vented via exhaust 13.

Mask flow may be measured by a flow sensor, such as a pneumotachograph and differential pressure transducer to derive a flow signal F(t). Alternatively, the pneumotachograph may be replaced by a bundle of small tubes aligned in parallel with the flow from the blower with the pressure difference measured by the differential pressure transducer across the bundle.

Mask pressure is preferably measured at a pressure tap using a pressure transducer to derive a pressure signal $P_{mask}(t)$. The pressure sensor $4p$ and flow sensor $4f$ have been shown only symbolically in FIG. 1 since it is understood that those skilled in the art would understand how to measure flow and pressure.

Flow F(t) and pressure $P_{mask}(t)$ signals are sent to a controller or microprocessor—referred to herein as processor 15—to derive a pressure request signal $P_{Request}(t)$. The controller or processor is configured and adapted to perform the methodology described in more detail herein. The controller or processor may include integrated chips, a memory, and/or other instruction or data storage mediums to implement the control methodology. For example, programmed instructions with the control methodology are either coded on integrated chips in the memory of the device, loaded as software, embedded as firmware, implemented as some combination thereof, etc. As those skilled in the art will recognize, analogue devices may also be implemented in the control apparatus.

The controller or processor 15 is further adapted to derive parameters indicative of the patient's breathing and sleep pattern, such as for deriving indications of flow limitation, such as flow flattening, snore, apnea and hypopnea and the Apnea Hypopnea Index (AHI), and for distinguishing between REM and non-REM sleep. See U.S. Pat. Nos. 5,704,345 and 6,029,665.

The apparatus of FIG. 1 includes other sensors, communication interfaces and displays, a servo, etc., and functional blocks the details of which are not necessary for an understanding of the present invention.

2. Acclimatization Therapy for First Time Users

Figure 2:
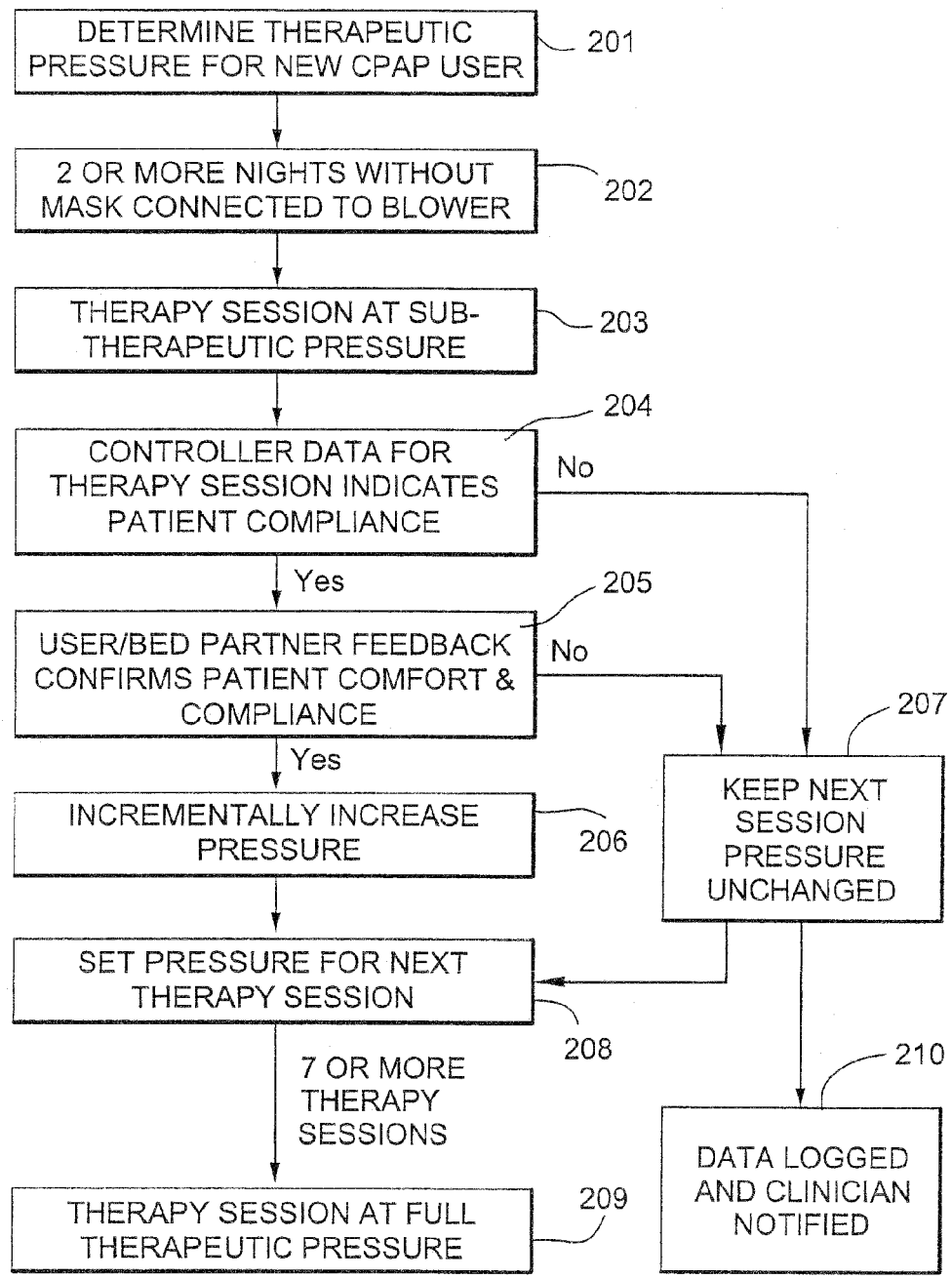
FIG. 2 is a flowchart illustrating an acclimatization therapy for new users of CPAP treatment according to an example embodiment.

FIG. 2 illustrates an acclimatization therapy for new users of CPAP therapy according to an example embodiment. After initial set up by a clinician, including setting of a full therapeutic pressure (step 201), the patient is sent home with a CPAP mask and blower.

2.1 Becoming Acclimatized to Headgear and/or a Mask

For the first few nights of the acclimatization therapy (e.g., two or more nights), the patient is provided with a headgear and mask from which the elbow and gas conduit have been disconnected, thus allowing the patient to first become accustomed to the feel of the mask and headgear during sleep, without additional impediments such as the noise and air pressure generated by the blower (step 202). In certain example embodiments, noise may be introduced in addition to, or in place of, wearing the headgear. For example, a recording may be played, a blower may be turned on with the mask left off the patient, etc.

2.2 Becoming Acclimatized to a Flow of Breathable Gas

For the next step in the acclimatization therapy, the elbow and gas conduit are connected to the mask, and the blower is turned on.

The blower is set to a "first timer mode" (also referred to herein as a "Max Ramp" or "AccliMATE" mode), in which the treatment pressure for the entire first CPAP session is provided at a sub-therapeutic pressure, for example at 2 cmH$_2$O (step 203).

Before the start of the second CPAP session, a series of pre-programmed patient and/or bed partner feedback questions are displayed on the machine display, the responses to which are used in setting the treatment pressure for the next session. For example, the patient may be asked to provide a yes/no answer, or a rating out of ten, to questions relating to treatment comfort, and the patient and/or the bed partner may be asked to respond to questions relating to patient restlessness and sleep quality.

If the patient and/or bed partner responses are sufficiently favorable to indicate that the patient is adjusting to the sensations of the therapy, and the recorded measurements of the treatment session indicate substantial patient compliance with the therapy (steps 204 and 205), the pressure for the next session is incrementally increased (step 206), e.g., by 1 cmH$_2$O. If the responses do not indicate patient acclimatization, or if other indicators of patient compliance for the session are negative (for example indicating that the patient removed the mask for a substantial period) (steps 204 and 205), the treatment pressure is not increased (step 207), e.g., pressure unchanged.

The pressure is set for the next therapy session (step 208), and the process of patient feedback and incremental increase in treatment pressure is repeated until full therapeutic pressure is reached, e.g., after 7 or more sessions (step 209). In the case of APAP treatment, once the treatment pressure reaches a therapeutic pressure of 4 cmH$_2$O, the treatment pressure may be a capped maximum pressure for the session. In the case of bilevel CPAP treatment, either just the inhalation (IPAP) pressure may be capped or both the IPAP and the exhalation (EPAP) pressure may be scaled down correspondingly. Further variations on APAP and bilevel CPAP treatment are described in more detail below.

If more than a predetermined number of successive—or cumulative—negative feedback responses are recorded, the controller will cause display of a message advising the patient to contact the clinician. If the device is connected to external communication, e.g., to the telephone network, the notification may be sent directly to the clinician e.g., data logged and clinician notified (step 210). Example processes for notifying the clinician are described in greater detail below.

Details of the patient feedback responses, and the treatment pressures may be stored in the controller for later review by the clinician.

In an example embodiment, the controller may be programmable by the clinician using the menu system to alter the parameters of the 'first timer' mode, for example, to set the initial therapy session pressure and/or the daily pressure increment according to the severity of the patient's sleep disordered breathing and the clinician's opinion of how long the patient may take to acclimatize to the sensations of the CPAP therapy.

The acclimatization therapy thus allows the patient to gradually adjust to the sensations of CPAP therapy, with the progression profile of the acclimatization controlled according to patient feedback. It is expected that adoption of this approach will increase the chance of patient compliance during the early stages of therapy, and therefore increase long-term acceptance and compliance.

Figure 3:
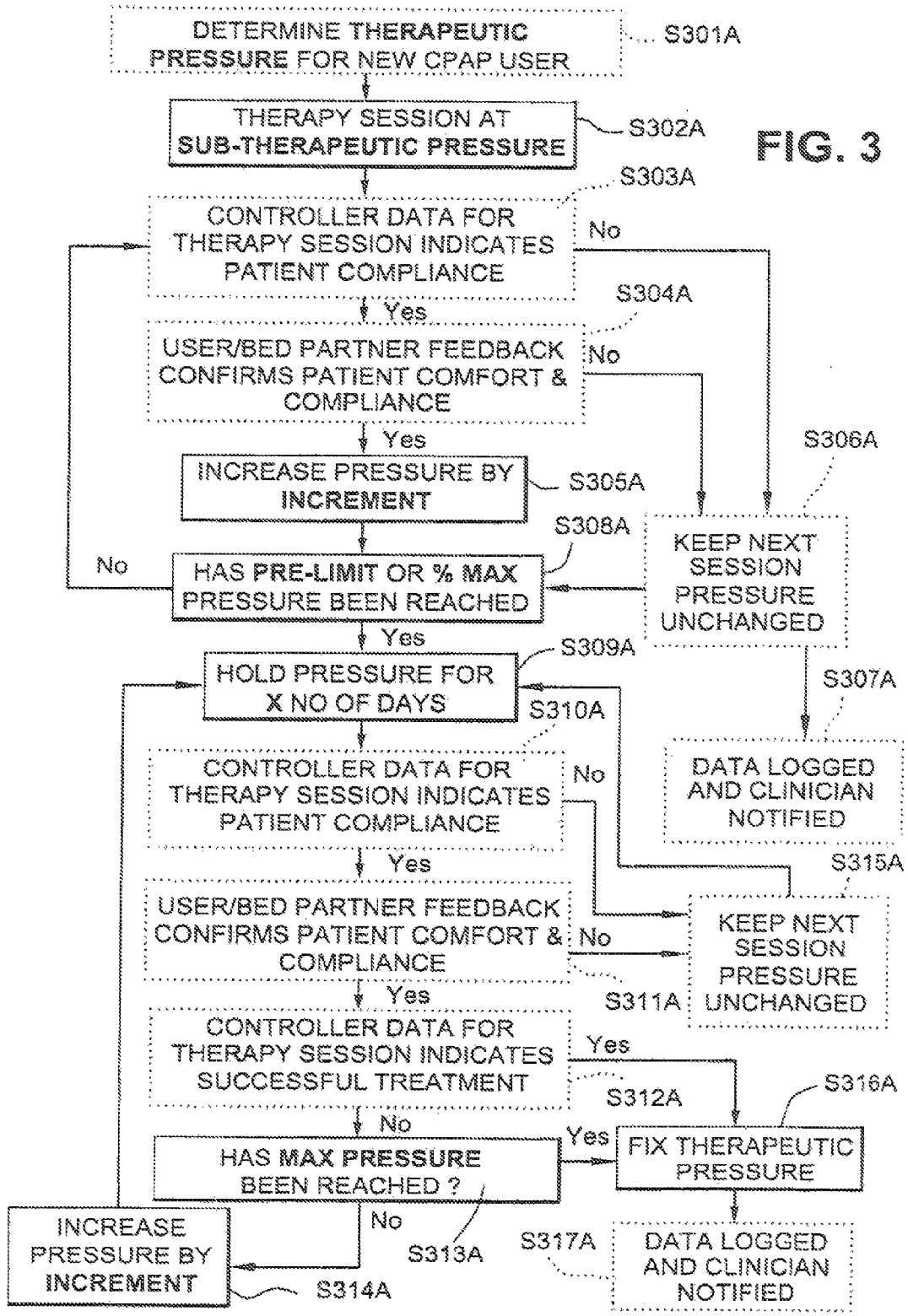
FIG. 3 is a flowchart of an acclimatization therapy for new CPAP users according to an example embodiment.

FIG. 3 illustrates a modified form of acclimatization therapy for first time CPAP users, which is adapted to help in setting of an appropriate maximum treatment pressure.

In the embodiment of FIG. 3, the clinically-derived full therapeutic pressure for the patient is determined by the clinician in a titration study (step 201A).

In the acclimatization therapy, the CPAP device includes a 'Max Ramp' feature which is programmed to hold a maximum pressure for a preprogrammed day number (step S309A) and monitor the patient's respiratory events via the device's monitoring capabilities, such as the ResTraxx™ function of ResMed machines to see if that pressure is the correct one. Steps S302A-S307A are similar to steps 203-207, and 210 of FIG. 2 described above. The maximum pressure is incrementally increased each day until a preset percentage or pressure differential from the titrated maximum pressure is reached (step S308A), and is held there (step S315A) or increased (step S314A) based on monitored treatment effectiveness, the presence/absence of respiratory events, clinician review, or may be based upon user/bed partner feedback, comfort and compliance (steps S310A, S311A, S312A) such as that illustrated in FIG. 2. Once maximum pressure is reached (step S313A) and/or therapy session indicates successful treatment (step S312A), the therapeutic pressure is fixed (step S316A) and data logged and clinician notified (step S317A).

For example, a new CPAP patient may be titrated in a sleep study and a maximum treatment pressure of 12 cmH$_2$O may be prescribed. On the first night of treatment the treatment ramps from 4 to 5 cm over the first 45 minutes of treatment. On the next night the pressure ramps up over 45 minutes from 5 cm to 6 cm and so on until it gets to within a predetermined amount—for example 4 cmH$_2$O—or a predetermined percentage—such as 80%—of the prescribed maximum treatment pressure. So in this example the CPAP machine may be programmed by the clinician to stop the daily increase at a pressure of 8 (i.e., 12-4) cmH$_2$O for a set number of days (e.g., up to 7 days) to monitor the patient airway using the monitoring functions of the CPAP machine. If the patient is not having adverse respiratory events at, for example, the pressure of 10 cm, then the maximum treatment pressure may be fixed at that level rather than progressing to the originally-prescribed level of 12. If the patient is still having adverse respiratory events at a pressure of 12, then the machine may increase it or refer the patient to the clinician for a decision on whether to increase the treatment pressure.

It is envisaged that this acclimatization therapy would give at least some of the benefits of the AutoSetting function of an AutoSet CPAP machine but would result in a fixed pressure that many Doctors/Clinicians are comfortable with rather than AutoSetting adjustment of the treatment pressure breath-by-breath. This keeps greater control of the set pressure in the hands of the clinician, which some patients and clinicians may be more comfortable with. This acclimatization may also be used as a stepping stone to getting patients and clinicians accustomed to AutoSetting functions.

In addition to the above techniques which may be used to help patients using CPAP devices prepare for treatment via AutoSet devices, AutoSet devices themselves may be configured to provide acclimatization therapy to a patient. For example, in certain example embodiments, in an AutoSet device, a first minimum pressure level may be initially provided. The minimum pressure level may be increased over time, for example, as defined in other parts of this disclosure. Alternatively, or in addition, the level of gain in pressure in response to an event may increase over time. For example, when an apnea is detected, a first pressure may be provided to treat it. For subsequent apneas (e.g. apneas 2 and 3), the pressure may be increased a predetermined amount, Apneas after these (e.g. apneas 4 and 5) may be treated with a pressure boost greater than the first predetermined amount. In particular, a first apnea (or a first group of apneas) may be treated by increasing the pressure 0.5 cmH$_2$O/minute, whereas a second apnea (or a second group of apneas) may be treated by increasing the pressure 1 cmH$_2$O/minute.

Figure 4:
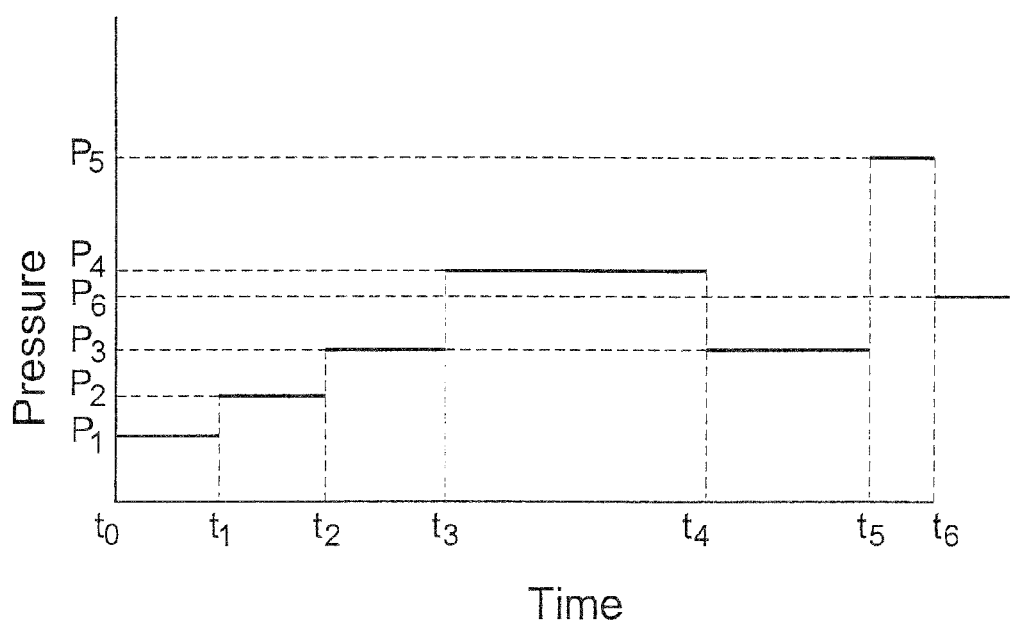
FIG. 4 is an illustrative pressure vs. time graph for acclimatization therapy with an AutoSet device in accordance with an example embodiment.

FIG. 4 helps to illustrate several possibilities that may arise when such example embodiments are implemented. FIG. 4 is an illustrative pressure vs. time graph for acclimatization therapy with an AutoSet device in accordance with an example embodiment. In FIG. 4, the AutoSet device provides a supply of breathable gas at a minimum pressure $P_1$ from time $t_0$ to $t_1$. The minimum pressure is increased a predetermined amount to pressure $P_2$ from time $t_1$ to $t_2$. The minimum pressure again is increased a predetermined amount to pressure $P_3$ from time $t_2$ to $t_3$. At time $t_3$, an apnea is detected. Accordingly, the pressure is boosted a predetermined amount to $P_4$. When the apnea is normalized at time $t_4$, the pressure drops to its previous minimum level, $P_3$. Another apnea event is detected at time period $t_5$, and the pressure is boosted to $P_5$. The amount of the pressure boost from $p_4$ to $p_5$ is greater than the amount of the pressure boost was from $P_3$ to $P_4$. For example, $P_5=(P_4-P_3)+\delta$, where $\delta$ is a incremental change in the gain provided during an obstructive event. When the apnea is normalized at time $t_6$, the pressure reduces to a new minimum pressure level, $P_6$.

2.3 Increased Clinician Control Over Treatment and Treatment Parameters

In the flowchart of FIG. 3, those items in bold may be preset or prescribed by the clinician (e.g., initial sub-therapeutic pressure, increment pressure, max pressure, pre-limit or % of max pressure, X no. of days to hold at pre-limit or % of max pressure, no. of events or other criteria that indicates successful treatment). Those boxes in dashed lines may optionally be omitted.

Possible advantages of the acclimatization therapy of FIG. 3 include improvement in the treatment of patients where the prescribed pressure is too high or too low, with consequent reduction in therapist's time treating those patients. Such patients currently take a substantial amount of therapist's time for treatment because they are being over treated or under treated and furthermore these patients are often not happy/compliant. The stair stepping approach of the 'Max Ramp' feature could cut the costs of treatment of such patient by helping to determining the appropriate pressure with minimal therapist intervention. The method may be carried out with modifications based on a ResMed Elite machine or a ResMed ResTraxx machine, both of which are less expensive machines than one having full AutoSet capabilities. If the prescribed pressure was determined to be wrong, the home medical equipment (HME) provider could send the patient a card to change the pressure; simple and cost effective. Also, the method includes minimal work from the patient, which helps to achieve new patient compliance and acceptance of the treatment.

A further embodiment of the invention provides a simplified acclimatization therapy ("Max ramp") mode with greater control by the clinician.

In this embodiment, the machine is programmable to increase the maximum treatment pressure automatically over time. The Clinician could program the start pressure, for example, 4 cm, and have the device ramp up to the prescribed pressure over a set period of time with no patient involvement.

For example, start pressure may be set at 4 cmH$_2$O and maximum pressure set at 10 cmH$_2$O. The clinician could prescribe a Max Ramp of 6 days. On Day 1 the device would start at 4 cmH$_2$O and stay at 4 cmH$_2$O all night. On day 2 the device would start at 4 cmH$_2$O and ramp, depending on the set ramp time (max 1 hour), to 5 cmH$_2$O and stop. Day 3 start at 4 cmH$_2$O and ramp to 6 cmH$_2$O, and so on, until the set maximum therapeutic pressure is reached.

The clinician would choose the number of days the Max ramp was to occur and the device would calculate the daily increase in a linear or other predetermined fashion. Alternatively the clinician could set the start pressure and start Max Ramp feature. For example, start pressure 4 cmH$_2$O and stop at the start Max Ramp Feature of 7 cmH$_2$O, max pressure=12 cmH$_2$O. In this scenario, day one the device would start at 4 cmH$_2$O, ramp to 7 cmH$_2$O over the ramp time (max 1 hour) then hold there for the first night. On day 2 the device would start at 4 cmH$_2$O, ramp (max 1 hour) to 8 cmH$_2$O (or what ever the linear calculation says, and stop) and so on throughout the set time for the Max Ramp.

2.3 Compliance Monitoring and Treatment Adjustment

Optionally, the clinician could choose a machine mode which allows the patient to hold at a pressure for an additional night if the patient feels the pressure is becoming too much. This could be accomplished by pressing a sequence of buttons on the device. This machine mode also allows programming by the clinician to set boundary conditions on the acclimatization therapy ("Max ramp") mode.

For example, the machine display may prompt the patient at the end of each daily session to enter a response indicating how they coped with the therapy. The patient could press "Okay" or "Not okay". If many subsequent days are "okay", the machine increases the daily ramp increment to ramp to prescribed maximum therapy pressure more aggressively, thus bringing the patient to therapy as early as possible. If the patient responses indicate that the patient is struggling to acclimatize to therapy (e.g. two consecutive days of "Not Okay"), the daily ramp increment is decreased to extend the acclimatization period, within the clinician-set boundaries.

More than a preset number of daily "Not okays" may cause the device to prompt the patient with help details (visual and/or audible methods) and/or request patient to contact clinician before getting too frustrated with the therapy, thus potentially reducing drop-outs even further.

Alternatively, or in addition to gathering such information, certain example embodiments may include a compliance monitoring package. This compliance monitoring package may monitor one or more parameters associated with a patient's comfort level and/or compliance level with respect to the device. For example, monitored parameters may include changes in the patient's Apnea-Hypopnea Index (AHI), changes in the leak level, the number of "mask off" events, etc. As noted above, the device may accordingly provide assistance in overcoming potential problems, or suggest calling the physician (e.g. by displaying such information to the patient, etc.). In one example embodiment, once compliance data has been captured, diagnoses may be made by the compliance monitoring package by comparing any compliance data to identifiable problems or preprogrammed problem heuristics (e.g. repeated mask off events may correspond to a poor fit, a very restless sleeper, etc.). If problems are identified, a database of suggested solutions may be referenced. The appropriate solutions may then be displayed, or, if no solutions exist, the compliance monitoring package may suggest a visit to the sleep lab. It will be appreciated that the compliance monitoring package may include hardware, software, firmware, and/or a combination thereof. For example, a hardware sensor may be required to measure leak, while software may compute the patient's AHI. As another example, the compliance monitoring package may be embodied in a series of instructions included in the processor or controller of a flow generator. However, it will be appreciated that such configurations are presented by way of example and without limitation. It also will be appreciated that such compliance monitoring packages may be used with other acclimatization techniques, such as, for example, those described herein. As a further example, a compliance monitoring package may be configured to work with the techniques described below with reference to FIG. 4A, such that acclimatization therapy may be provided (steps S402, S404, S406, and S407), and a patient may alone or with a physician use the illustrative compliance monitoring package described herein for diagnosis and further treatment. Thus, step S408 may communicate the information to a physician and/or the compliance monitoring package, and the adjustments of step S410 may be applied by the physician and/or the patient in response to output generated by the monitoring package.

Where the device has communication capabilities, the device may also contact the clinician directly to get into contact with the patient. For example, a commercially available system such as ResTraxx™ may allow a clinician at a remote location to monitor and/or alter the patient's therapy. It will be appreciated that such remote monitoring may be performed automatically (e.g. reports may be sent periodically, when problems are detected, etc.), or it may allow a clinician to choose when to retrieve data via one or more communicators.

Figure 4A:
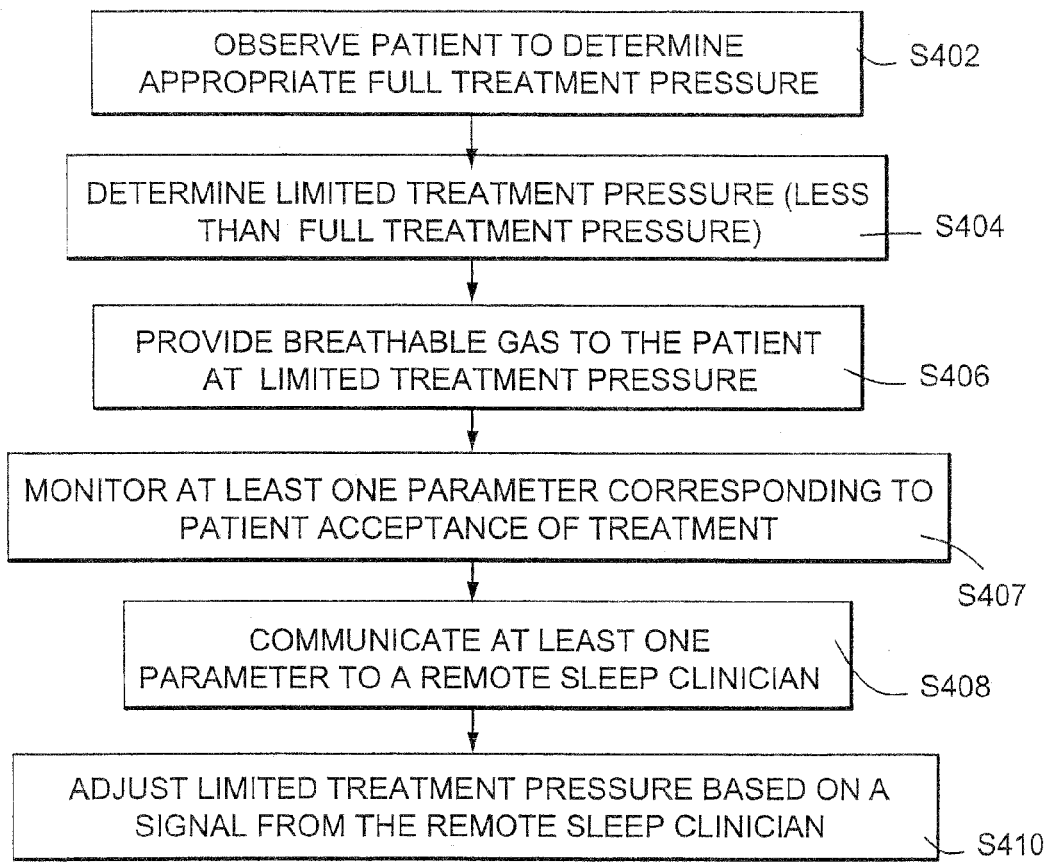
FIG. 4A is a flowchart illustrating a process for remotely controlling acclimatization therapy in accordance with an example embodiment.

In particular, FIG. 4A is a flowchart illustrating a process for remotely controlling acclimatization therapy, in accordance with an example embodiment. In step S402, at least one parameter of the patient is observed to determine an appropriate full treatment pressure. In step S404, a limited treatment pressure less than the full treatment pressure is set. Then, in step S406, breathable gas is provided to the patient at the limited treatment pressure. Parameters corresponding to patient's acceptance of the treatment are monitored in step S407 and communicated to a sleep clinician remote from the patient in step S408. Optionally, in step S410, the limited treatment pressure may be adjusted based on a signal from the remote sleep clinician.

Other techniques may be used to allow clinicians to alter treatment parameters and/or store data relating to the treatment (e.g. information relating to how well a patient is acclimatizing to a treatment, the extent to which the treatment is successful, etc.). According to an example embodiment, a treatment device may be configured to read data embedded on one or more smartcards. Each smartcard may have a set of treatment parameters embedded thereon, and thus, different smartcards may be appropriate for different conditions. For example, one series of smartcards may be appropriate for treating snore, and another series may be appropriate for treating apneas. It will be appreciated that other configurations also are possible, and the examples are provided for non-limiting, illustrative purposes.

With regard to acclimatization in particular, a series of smartcards may, for example, be programmed to provide increasing breathing gas pressures. Thus, as a patient replaces cards, the pressures may be stepped up. In certain example embodiments, the smartcards may function only for a predetermined period (e.g. one night, one week, etc.) or a predetermined number of uses (e.g. once, twice, etc.). Thus, the smartcards may, for example, prevent a patient from reverting to lower pressures (e.g. pressures that the patient may have already become acclimatized to and thus confer little or no therapeutic advantage), thus progressing the acclimatization. It also may help ensure that patients receive follow-up diagnoses as a specific sleep study or course of treatment concludes, etc.

It will be appreciated that the smartcards also may store treatment-related data, as monitored by the device, inputted by the patient, etc. This data may be retrieved by a clinician, for example, to track a patient's acclimatization and/or treatment progress, revise prescribed therapies, etc.

Figure 5:
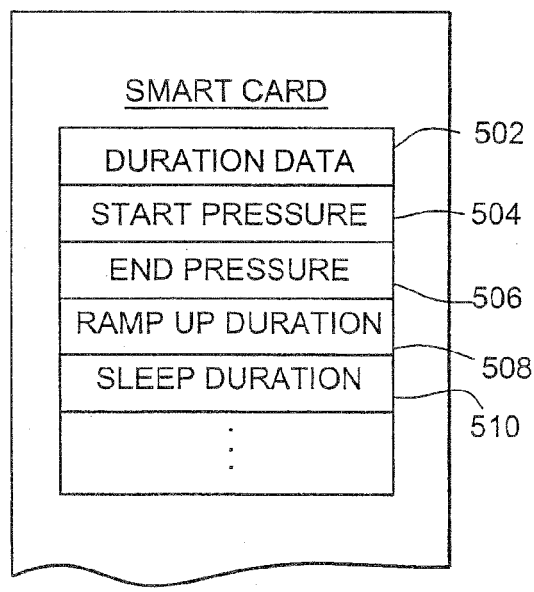
FIG. 5 is an illustrative view of a memory map embedded in a smartcard in accordance with an example embodiment.

FIG. 5 is an illustrative view of a memory map embedded in a smartcard in accordance with an example embodiment. Duration data is stored in area 502. Duration data may include information, such as, for example, the number of times certain settings may be used, a time period during which the smartcard is operable, etc. Area 504 indicates a pressure at which the therapy should begin, while area 506 indicates a target or end pressure that the therapy should reach. Area 508 includes ramp up data (e.g. how long a ramp up period should last, how fast the pressure should ramp up, etc.). Area 510 indicates how long the patient's sleep should last (e.g. 8 hours, etc.). It will be appreciated that other data may be embedded in the smartcard in place of, or in addition to, the data shown. It also will be appreciated that certain areas of the data may be writeable to store parameters (e.g. acclimatization data, number of uses, etc.).

3. Further Variations on Acclimatization Therapy Techniques

3.1 Treatment During Awake Settling Times

According to an example embodiment, a first pressure (or first set of pressures) may be provided in the period during which the patient is falling asleep, and a second pressure (or second set of pressures) may be provided while the patient is asleep. This or similar techniques may be used as an alternative to certain other example embodiments which, as described above, may deliver sub-therapeutic pressures throughout the night and ramp up pressures over a number of nights, which thereby delays the time until the full pressure is delivered until a later point during the therapy.

More particularly, a low pressure level may be delivered during an awake settling time. This low pressure level may be delivered for a predetermined amount of time (e.g. fifteen minutes, thirty minutes, one hour, etc.). Thus, the patient may become acclimatized to receiving at least some pressurized gas before the full therapeutic level is delivered during the course of the night. Following this predetermined time limit, the device may ramp up to the full therapeutic pressure. Optionally, the length of time of the ramp up during the sleep phase may be selected. According to an example embodiment, the initial pressure delivered during the settling time may ramp up over several days, for example, reducing the amount of time a patient before the full treatment pressure is delivered.

Figure 6A:
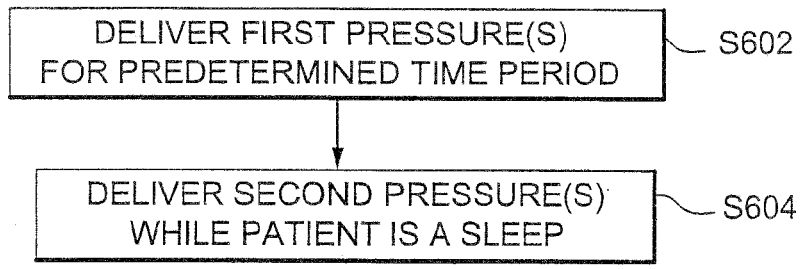
FIG. 6A is an illustrative flowchart in which different pressures are provided for the period in which a patient is falling asleep and the period in which the patient is asleep.

FIG. 6A is an illustrative flowchart in which different pressures are provided for the period in which a patient is falling asleep and the period in which the patient is asleep. In step S602, a first pressure or first set of pressures is/are delivered for a predetermined time period. This first time period corresponds to treatment while the patient is falling asleep, and there may be a ramp up during this period. In step S604, a second pressure or second set of pressures is/are delivered while the patient is asleep. Again, the pressures may ramp up at this time.

The predetermined time limit may reflect the amount of time it takes for the patient to fall asleep. In an example embodiment, the device may comprise a "snooze button" to allow the patient to prolong the awake settling period by an additional predetermined amount of time (e.g. 10 minutes, 15 minutes, 30 minutes, etc.). It will be appreciated that the "snooze feature" relates to the comparative inactivity of the device, rather than the state of the patient. Alternatively, the snooze feature may be thought of as providing an additional amount of time needed to allow the patient to begin "snoozing." Thus, the patient may extend the delay before the ramp up period begins if the patient does not fall asleep during the initial predetermined time. In certain example embodiments, a device may store how many times a patient pushes the snooze button. Based on this data, the device may "learn" how long it takes a patient to fall asleep and adjust the initial predetermined time amount accordingly. Thus, in response to this "preferred settling time," the device may adjust an initial ramp up period (e.g. during the settling time) or the ramp up period during sleep accordingly. Similarly, as the patient acclimatizes to the therapy, the awake settling time may be reduced based on the recorded data. It will be appreciated that this technique may be used as a further refinement to certain example techniques described below which, in general, monitor the patient's sleep state and change the delivered pressure based on the sleep stage, possibly including whether the patient is asleep at all (e.g. one or more parameters for determining whether the patient is asleep may be monitored). Alternatively, it will be appreciated that this technique may be conceived of as a sub-classification of the below-described techniques. For example, illustrative sleep stages may include, for example, awake, falling asleep, REM sleep, NREM sleep, etc.

Figure 6B:
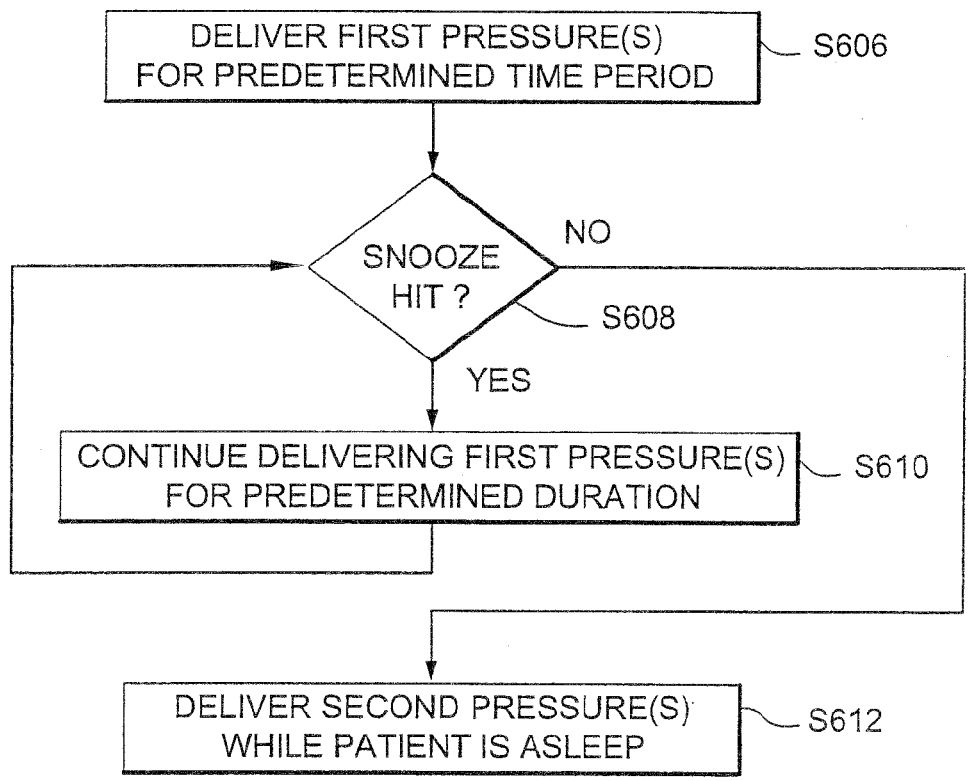
FIG. 6B is an illustrative flowchart in which different pressures are provided for the period in which a patient is falling asleep and the period in which the patient is asleep, taking into account a mechanism for delaying transition to the sleep period mode.

FIG. 6B is an illustrative flowchart in which different pressures are provided for the period in which a patient is falling asleep and the period in which the patient is asleep, taking into account a mechanism for delaying transition to the sleep period mode. Again, in step S606, a first pressure or first set of pressures is/are delivered for a predetermined time period. This first time period corresponds to treatment while the patient is falling asleep, and there may be a ramp up during this period. If the snooze button is hit in step S608, step S610 continues to deliver the first pressure or first set of pressures for a predetermined duration. If the snooze button is not hit in step S608, in step S612 a second pressure or second set of pressures is/are delivered while the patient is asleep. Again, the pressures may ramp up at this time.

3.2 Treatment According to Sleep Stage

Similar to delivering different pressures (or different sets of pressures) based on whether a patient is asleep, certain example embodiments may deliver different pressures based on sleep stage. Thus, a device may first determine the sleep stage a patient is in. Based on this determination, a suitable pressure may be delivered. For example, higher treatment pressures may be delivered during REM sleep as compared to NREM sleep (e.g. because REM sleep typically is characterized by a relatively considerable amount of body activity, whereas NREM sleep typically is characterized by progressive relaxation). Treatment parameters for each of the different stages of sleep may be preset by clinicians. Thus, the patient may receive therapeutic pressures at the sleep stages in which they are needed most. For example, the patient may not receive high pressures while they are awake (e.g. before falling asleep, while waking up after REM sleep, etc.). In such cases, the device may detect arousals and adjust the pressure accordingly.

Figure 7:
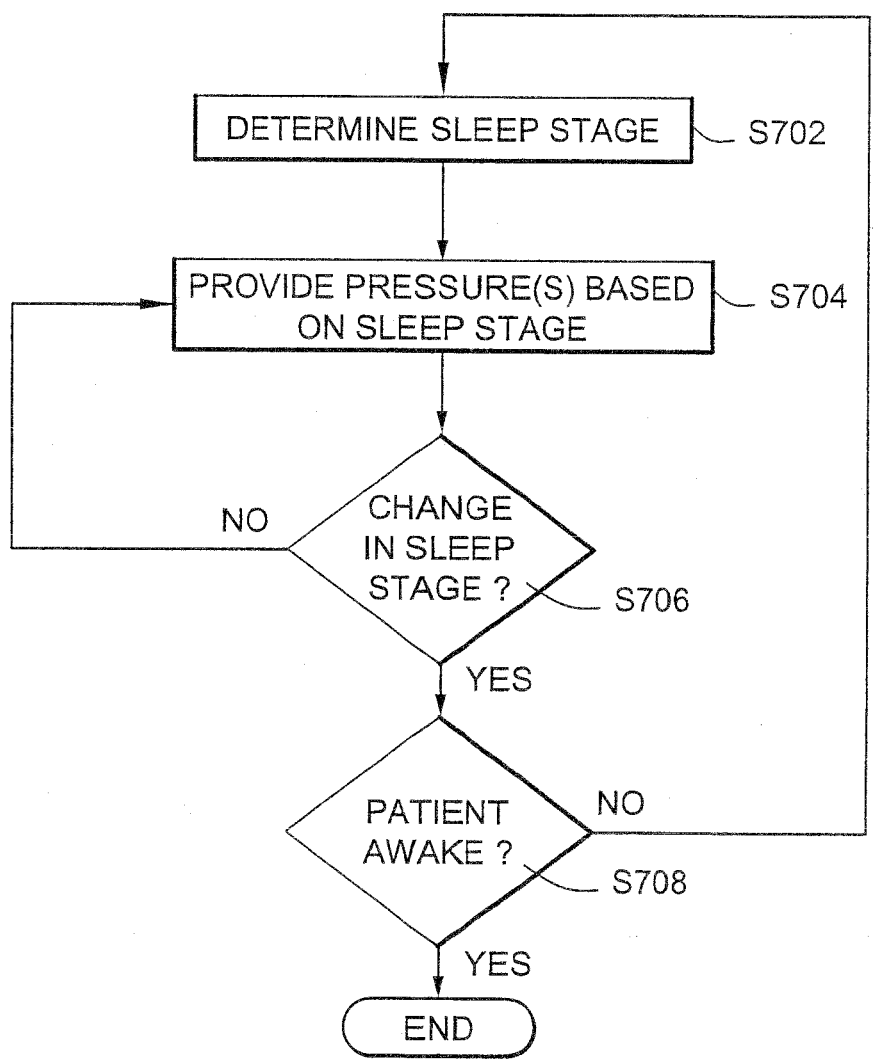
FIG. 7 is an illustrative flowchart showing a process for providing a set of pressures based on the patient's sleep stage in accordance with an example embodiment; and, FIG. 8 is an illustrative flowchart showing how a bilevel device can be made to provided CPAP therapy as a part of acclimatization therapy.

FIG. 7 is an illustrative flowchart showing a process for providing a set of pressures based on the patient's sleep stage in accordance with an example embodiment. The sleep stage the patient is in is determined in step S702. In step S704, a set of pressures is provided based on the sleep stage determined in step S702. If it is determined that the sleep change has not changed in step S706, the pressure levels are not changed. If the sleep state is changed, it is determined whether the patient is awake in step S708. If the patient is awake, the process is over. In this case, the supply of breathable gas may be stopped completely, reduced to a comfortable "awake pressure," etc. If the patient awakens briefly, the process may return to step S702 when the patient falls asleep again. However, if the patient is not awake, the process returns to step S702 to determine the new sleep stage and to provide an appropriate pressure in step S704. It will be appreciated that a treatment pressure may be provided initially at a limited pressure and then ramped up to a full treatment pressure associated with the particular sleep stage.

3.3 Using Bilevel Treatments to Acclimatize a Patient to Full CPAP Treatment

Regardless of the whether the patient is asleep and the type of sleep the patient is in, as noted above, some patients may not respond well to single-level CPAP therapy. An example acclimatization process may accordingly first provide bilevel therapy and transition to CPAP mode as the patient becomes acclimatized to the therapy. This process reflects the reality that some patients respond well to increased pressures during inhalation, but respond poorly during exhalation. Thus, a device may begin in bilevel mode, providing IPAP and EPAP therapies at distinct pressures. As the patient becomes more acclimatized to EPAP therapy, the pressure may be ramped up. When IPAP and EPAP parameters are substantially the same, CPAP therapy effectively will be administered. In certain example embodiments, the IPAP therapy may remain constant as the EPAP therapy is ramped up. Alternatively, IPAP and EPAP therapies both may be ramped up, but with IPAP and EPAP parameters being adjusted at different rates. For example, the IPAP may reach the target CPAP level more quickly because inhalation pressure may be accepted more easily. In cases where the IPAP and EPAP parameters are substantially the same but are nonetheless lower than the target CPAP parameters, they may be adjusted together or apart, depending, for example, on the particular patient, the acclimatization history, etc.

Figure 8:
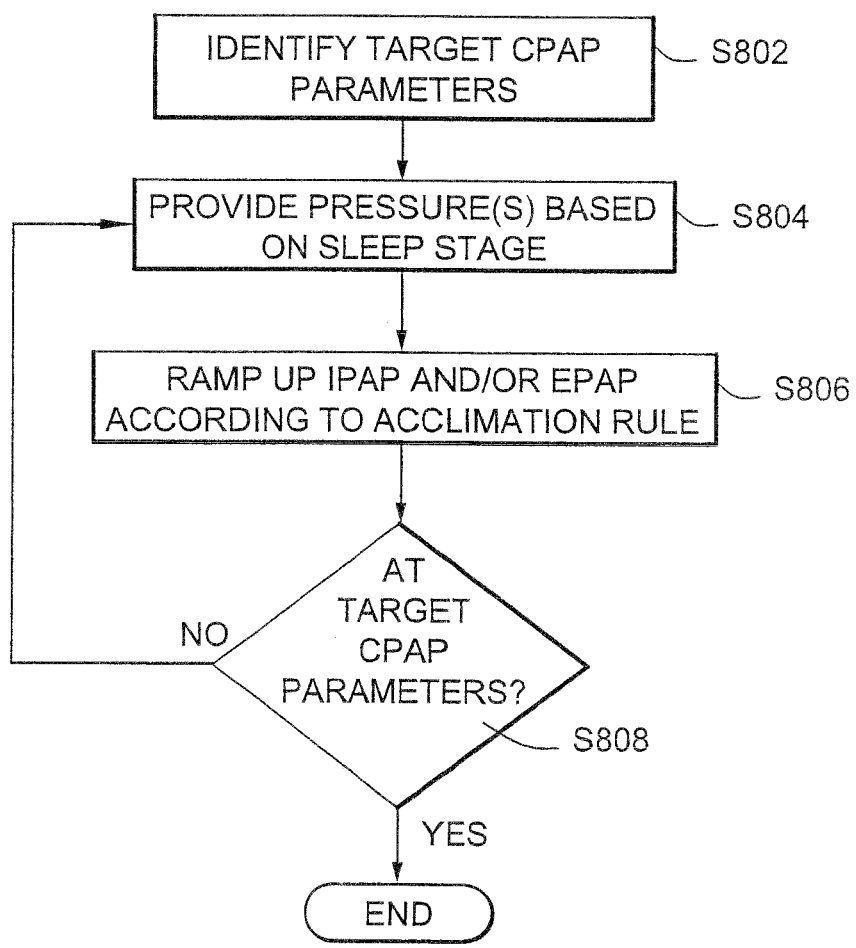

FIG. 8 is an illustrative flowchart showing how a bilevel device can be made to provided CPAP therapy as a part of acclimatization therapy. In FIG. 8, the target CPAP parameters (e.g. a pressure of breathable gas, etc.) is identified. A bilevel treatment below the target CPAP level is provided in step S804, with the treatment level potentially being based in part on sleep stage. IPAP and/or EPAP may be ramped up according to an acclimatization rule in step S806. For example, IPAP pressures may ramp up faster than EPAP pressures, but it may also reach a plateau more quickly than the EPAP therapy. Step S808 determines whether the device is functioning at the target CPAP level. If it is not, the bilevel treatment continues in step S804, and ramp ups may occur in step S806. If the target CPAP levels have been reached, the process is ended.

3.4 Example Software Modes and Settings

Further details of the process phases, the machine modes and an example of this embodiment are set out below.

A. Acclimatization Process Phases

The acclimatization therapy goes through three phases:
1. Initiation Phase: Physician or Clinician prescribes an "AccliMATE" mode
2. AcciMATE Phase: the AcciMATE mode automatically adjusts nightly CPAP pressure until final set-point CPAP pressure is reached according to physician or clinician
3. Standard CPAP Phase: Flow Generator Operates in Standard CPAP mode B. Acclimate Mode Detail 1. Physician/Clinician Adjustable Parameters:
  (a) Adjustment period (settable range): 1-30 days
  (b) End target CPAP setting ("T"): 4-20 cm H2O
  (c) Starting night #1 CPAP setting ("S"): 4-*H2O (can only be set where "S"<"T")
  (d) Optional patient "snooze" button function. When pressed by the patient this would maintain previous day's CPAP pressure setting for a physician/clinical set limited number of days at any individual pressure. Settable range=0-5 days. This snooze function can be turned off or can allow the patient to remain at any one pressure for a limited number of days if they push the "snooze' button at the beginning of the next night's session during the CPAP AccliMATE phase.

Note: standard nightly ramp from 4 cm H$_2$O to that night's set point can be set as normal from 0-45 minutes using standard ramp function 2. Machine calculation modes:
  (a) Linear
  (b) Logarithmic
  (c) Exponential
  (d) Step-function (0.5 cm/day, 1 cm/day, 2 cm/day, 3 cm/day, etc.)
  (e) Other formulae C. Example Clinician/Physician sets:
(a) Adjustment period=7 days
(b) End target CPAP 10 cm H2O
(c) Starting CPAP=4 cm H2O
(d) Patient Snooze=0 days (i.e., off)

| | Day # | | | | | | |
|---|---|---|---|---|---|---|---|
| | 1 | 2 | 3 | 4 | 5 | 6 | 7 |
| CPAP | 4 cmH$_2$O | 5 cmH$_2$O | 6 cmH$_2$O | 7 cmH$_2$O | 8 cmH$_2$O | 9 cmH$_2$O | 10 cmH$_2$O |

In an alternative embodiment, a continuous ramp may be used throughout the entire acclimatization period rather than using incremental ramp sessions (e.g., up to 1 hour) to increase the pressure and then maintaining a lower pressure level for the remainder of the therapy session.

For example, the clinician may set the start pressure at 4 cmH$_2$O and the final treatment pressure of 12 cmH$_2$O with a MAX Ramp of 5 days. The device would continuously increase the pressure throughout the 5-day period. The machine would calculate the required rate of increase based on a predetermined formula. Alternatively, the clinician may set the rate of increase instead of the number of days for the MAX Ramp.

In an example, on day 1, start CPAP pressure (P1) would be 4 cmH$_2$O and the end CPAP pressure would be P2 wherein P2 is >4 cmH$_2$O but <12 cmH$_2$O depending on the time of use of the first night. On day 2, the start CPAP pressure would be P2 and the end CPAP pressure would be P3. On day 3, the start CPAP pressure would be P3 and the end CPAP pressure would be P4, and so on until pressure reaches the final treatment pressure, e.g., 12 cmH$_2$O.

In another embodiment, therapy may be started at full therapeutic pressure, and then after identifying a problem indicating that the patient is not coping at that pressure, decreasing the pressure to a lower level for a predetermined amount of time. The patient may identify a problem by inputting this into the device or the device may detect when a patient is having trouble with therapy and adjusting to compensate. For example, the device may measure the number of mask off events over time or the level of leak. In an embodiment, the initial start pressure of the therapy is determined based on inputs from the patient. The patient may provide an indication of how they cope with new things. The pressure would progressively increase back up to therapeutic pressure.

In yet another embodiment, the slow ramp or Acclimate mode may be controlled by the patient in that the patient may choose to either increase the pressure by a single increment upon commencing each new therapy session (or after each predetermined time period) or going directly to full therapeutic pressure. Thus, the increment is not automatic. A default back to full therapeutic pressure would prevent patients from continuing using the device sub-therapeutically for too long. In an embodiment, the device may learn the patients preference (e.g., increase every night or only every second night) and take over increasing the therapy pressure.

Each of the above described embodiments describes various alternative methods to assist in acclimatizing a patient to therapy or making therapy more comfortable for first time users. This boosts patient compliance and long term therapy.

Methods may include automatic methods where the device controls the entire process, semi-automatic methods where the patient interacts with the device to cause the machine to change parameters, and mechanical methods where the parameters are changed via a mechanical means rather than software.

3.5 Mechanical Methods for Changing Delivered Pressure Levels

In certain example embodiments, the pressure may be adjusted to acclimatize the patient to therapy by using the flow generator to control the pressure delivered. However, certain example embodiments provide user-controlled, mechanical processes for adjusting the pressure during patient acclimatization by, for example, controlling the level of leak in the patient circuit. Conventionally, mask leak is thought of as being disadvantageous, or, at a minimum, a factor that must be accounted for when administering a treatment. However, as a part of the acclimatization process, controlling the level of leak in the patient circuit may alter the delivered therapy level.

Thus, a vent or opening may be located on a mask to purposely allow for some leak. Then, the vent or opening may be progressively closed. As the opening becomes smaller, the leak will decrease and the delivered pressure will increase accordingly. By carefully choosing the size of the openings, it will be appreciated that the amount of leak may be reduced (and thus the delivered pressure may be increased) according to a scale (e.g. a linear scale, an exponential scale, etc.).

In certain example embodiments, it may be advantageous to allow the vent to be adjusted in one direction only, thus preventing a patient from reverting to a lower pressure level and thereby potentially slowing (or reversing) the acclimatization process. In certain example embodiments, a dial having protrusions capable of engaging with pre-formed recessions may be rotated to provide this form of mechanical leak control system. However, it will be appreciated that other suitable mechanical modifications may be made to a mask, and that the rotating dial is provided by way of example and without limitation. One mask system that may be used with these techniques is disclosed in U.S. application Ser. No. 10/579,221, entitled "Vent System for CPAP Patient Interface Used in Treatment of Sleep Disordered Breathing," filed May 12, 2006 and assigned to ResMed, which is a national stage application of PCT AU/04/01650 filed on Nov. 25, 2004, the entire contents of each of which is incorporated herein by reference.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise, comprised and comprises" where they appear.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each aspect, feature, or step of any example embodiment alone may constitute an additional embodiment of the present invention. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A continuous positive airway pressure (CPAP) apparatus for treatment of sleep apnea, the apparatus comprising:
   a housing;
   a display disposed in the housing;
   a blower configured to deliver a flow of pressurized breathable gas at positive air pressure between about 4 and 20 cmH$_2$O to a patient;
   at least one sensor that is set to detect a measured pressure and/or flow that is associated with the pressurized breathable gas;
   at least one controller that is communicably connected to the blower and the at least one sensor, the controller configured to:
      detect at least one of: 1) sleep flow limitation, 2) hypopnea, and/or 3) apnea based on the measured pressure and/or flow;

communicate with the blower to auto-adjust the flow and/or pressure of the pressurized breathable gas based on a determined breathing and/or sleep pattern of the patient;

communicate with the blower to ramp the pressure of the pressurized breathable gas over a period of time;

determine a sleep stage of the patient;

responsive to determination of a sleep stage of the patient and based on which sleep stage was determined, communicate with the blower to control a first ramping, which occurs over multiple breathing cycles of the patient, of pressure of the flow of pressurized breathable gas that is applied to the patient during inspiration; and responsive to determination of a sleep stage of the patient and based on which sleep stage was determined, communicate with the blower to control a second ramping, which occurs over multiple breathing cycles of the patient, of pressure of the flow of pressurized breathable gas that is applied to the patient during expiration, wherein the first and second ramping are different.

2. The apparatus of claim 1, further comprising a communication interface that is structured to interface with a portable non-transitory storage medium.

3. The apparatus of claim 1, further comprising a breathing tube to extend from the housing to a patient interface or mask.

4. The apparatus of claim 1, wherein the controller is further configured to:

determine whether the patient has transitioned from a sleeping state to an awake state; and communicate with the blower to decrease a pressure of the flow of pressurized breathable gas to the patient based on the determined transition from the sleeping state to the awake state.

5. The apparatus of claim 4, wherein the decreased pressure that is based on the determined transition is substantially no pressure or a comfortable awake pressure for the patient.

6. The apparatus of claim 4, where the blower is further configured to control the flow of pressurized breathable gas to the patient based a second transition from the awake state to the sleeping state.

7. The CPAP apparatus of claim 1, wherein the second pressure is set higher than the first pressure.

8. A continuous positive airway pressure (CPAP) apparatus for treatment of sleep apnea, the apparatus comprising:

a flow generator configured to deliver a flow of pressurized breathable gas at positive air pressure between about 4 and 20 cmH$_2$O to a patient wearing a patient interface device;

at least one pressure and/or flow sensor configured to generate signals of pressure and/or flow based on sensed physical quantity; and at least one electronic controller electrically coupled to the flow generator and the at least one sensor, the controller configured to:

determine a sleep stage of the patient based on a breathing parameter indicative of the sensed physical quantity;

communicate with the flow generator to control, based on the determined sleep stage, a pressure of the breathable gas that is delivered during inspiration of the patient in a first manner; and communicate with the flow generator to control, based on the determined sleep stage, a pressure of the breathable gas that is delivered during expiration of the patient in a second manner that is different from the first manner, wherein a difference between the first and second manner includes applying different pressure ramp characteristics, over multiple breathing cycles by the patient, to the controlled expiration and inspiration pressure of the breathable as that is delivered to the patient.

9. The CPAP apparatus of claim 8, further comprising a breathing tube that extends from the flow generator to a patient interface or mask.

10. The CPAP apparatus of claim 8, wherein the electronic controller is further configured to:

determine whether the patient has transitioned from a sleeping state to an awake state; and communicate with the flow generator to decrease a pressure of the flow of pressurized breathable gas to the patient based on the determined transition from the sleeping state to the awake state.

11. The CPAP apparatus of claim 10, wherein the decreased pressure that is based on the determined transition from the sleep to awake state is substantially no pressure or a comfortable awake pressure for the patient.

12. The CPAP apparatus of claim 8, wherein the at least one electronic controller is further configured to:

responsive to determination of the sleep stage, set a target pressure, wherein the pressure ramp characteristics applied according to the first manner ramp more quickly to the target pressure than the pressure ramp characteristics applied according to the second manner.

13. The CPAP apparatus of claim 8, wherein determination of a sleep stage includes determination of a transition from another sleep stage, the at least one electronic controller further configured to:

responsive to the determination of the transaction from another sleep stage, set an initial pressure for the pressurized breathable gas that is delivered to the patient, wherein the pressure of the breathable gas that is delivered during inspiration and the pressure of the breathable gas that is delivered during expiration are ramped to a target pressure based on respective pressure ramp characteristics.

14. The CPAP apparatus of claim 8, wherein the pressure ramp characteristics cause pressure to plateau more quickly for inspiration than expiration.

15. A continuous positive airway pressure (CPAP) apparatus for treatment of sleep apnea, the apparatus comprising:

a flow generator configured to deliver a flow of pressurized breathable gas at positive air pressure between about 4 and 20 cmH$_2$O to a patient wearing a patient interface device;

at least one pressure and/or flow sensor configured to sense a physical quantity related to delivery of the pressurized breathable gas; and at least one electronic controller electrically coupled to the flow generator and the at least one sensor, the controller configured to:

determine a sleep stage of the patient based on signals received from the at least one pressure and/or flow sensor;

in response to determination of a transition to a new sleep stage, automatically control a pressure level of the supplied pressurized breathable gas based on the determined sleep stage; and in accordance with determination of the transition to the new sleep stage, set a target expiration pressure level and a target inspiration pressure level, wherein pressure level of the supplied pressurized breathable gas during inspiration is ramped, over multiple breathing cycles of the patient differently to the target inspiration pressure level than how the pressure level of the supplied pressurized breathable gas is ramped, over the multiple breathing cycles of the patient, to the target expiration pressure level.

16. The CPAP apparatus of claim 15, wherein the target expiration pressure level or the target inspiration pressure level is higher than an initial pressure level.

17. The CPAP apparatus of claim 15, wherein the ramp to the target inspiration pressure level is faster than the ramp to the target expiration pressure level.

* * * * *

UNITED STATES PATENT AND TRADEMARK OFFICE
CERTIFICATE OF CORRECTION

PATENT NO.        : 9,440,037 B2  
APPLICATION NO.   : 13/961483  
DATED             : September 13, 2016  
INVENTOR(S)       : Mulcahy et al.

Page 1 of 1

It is certified that error appears in the above-identified patent and that said Letters Patent is hereby corrected as shown below:

In the Claims

In Claim 8, Column 20, Line 8, "pressure of the breathable as that is delivered to the" should be corrected to ---pressure of the breathable gas that is delivered to the---

Signed and Sealed this  
Twenty-first Day of February, 2017

Michelle K. Lee  
*Director of the United States Patent and Trademark Office*